United States Patent [19]

Cole et al.

[11] Patent Number: 4,948,575
[45] Date of Patent: Aug. 14, 1990

[54] ALGINATE HYDROGEL FOAM WOUND DRESSING

[75] Inventors: Susan M. Cole; James E. Garbe, both of St. Paul, Minn.

[73] Assignee: Minnesota Mining and Manufacturing Company, St. Paul, Minn.

[21] Appl. No.: 301,312

[22] Filed: Jan. 24, 1989

[51] Int. Cl.$^5$ ..................... A61L 15/42; A61L 25/00
[52] U.S. Cl. ..................... 424/44; 424/445; 424/DIG. 13; 424/43; 128/156
[58] Field of Search ............... 128/156; 424/444, 445, 424/619, 715, 722, DIG. 13, 43, 44; 523/111, 113; 604/304

[56] References Cited

U.S. PATENT DOCUMENTS

| | | | |
|---|---|---|---|
| 2,688,586 | 9/1954 | Eberl et al. | 424/445 |
| 4,291,025 | 9/1981 | Pellico | 424/180 |
| 4,391,799 | 7/1983 | Mason, Jr. et al. | 424/132 |
| 4,393,048 | 7/1983 | Mason, Jr. et al. | 424/132 |
| 4,401,456 | 8/1983 | Connick, Jr. | 71/88 |
| 4,613,497 | 9/1986 | Chavkin | 424/44 |
| 4,704,113 | 11/1987 | Schoots | 604/379 |

FOREIGN PATENT DOCUMENTS

| | | | |
|---|---|---|---|
| 92329 | 10/1983 | European Pat. Off. | 61 K/6/10 |
| 424956 | 8/1982 | Sweden | 61 L/15/01 |
| 2182663 | 5/1987 | United Kingdom | C08J/9/00 |

OTHER PUBLICATIONS

Davis et al., "In Vitro Evaluation of Alginate Gel Systems as Sustained Release Drug Delivery Systems", J. of Controlled Release, vol. 3, (1986), pp. 167-175.

Primary Examiner—Randall L. Green
Assistant Examiner—Paul Prebilic
Attorney, Agent, or Firm—Donald M. Sell; Walter N. Kirn; Gregory A. Evearitt

[57] ABSTRACT

A dimensionally stable alginate hydrogel foam wound dressing that absorbs wound exudate without any appreciable swelling. The wound dressing is formed-in-place in the wound cavity or on the wound surface from a reactive composition that foams as it gels. The water-insoluble alginate hydrogel foam based wound dressing is made by mixing together the ingredients of a two component system; applying the resulting composite liquid mixture to a wound site; and allowing the composite mixture to react. One component contains an aqueous suspension of certain di-or trivalent metal salts and an effervescent compound. The second component contains an aqueous solution of a biocompatible, water-soluble acid. At least one compound, and preferably both, contain a water soluble alginate.

27 Claims, No Drawings ured, clinical testing has established that the healing of a wound is enhanced by keeping the wound bed moist. Thus a wound dressing should absorb and transfer wound exudate away from the wound surface without desiccating the wound bed. Additionally, the wound dressing should release from the wound easily without causing damage to the newly formed tissue.

ALGINATE HYDROGEL FOAM WOUND DRESSING

TECHNICAL FIELD

The invention relates to wound dressings formed of alginate hydrogel foams and to the use of such dressings both for keeping a wound bed moist and contamination free, and for packing a deep wound.

BACKGROUND OF THE ART

Alginate fibers are well known and widely used in wound dressing materials. For example, a knitted alginate is currently being marketed as Ultraplast TM styptic gauze wound dressing by Wallace, Cameron & Co. Ltd., Glasgow, Scotland. Furthermore, a carded web of alginate fibers is being marketed as Steriseal Sorbsan TM surgical dressing by N.I. Medical, Redditch, Worcestershire, England, and a carded and needle-tacked web of alginate fibers is being marketed as Kaltostat TM hemostatic wound dressing by Cair Ltd., Aldershot, Hatt, England. Additionally, alginate tow is marketed by each of the latter two companies under the same tradenames for use as wound dressings and surgical packings.

It is stated in U.S. Pat. No. 4,704,113 (Schoots) that two important functions of surgical or wound dressings are the ability to absorb and hold liquid and the ability to wick and transfer exudate of a wound away from the wound site. Furthermore, clinical testing has established that the healing of a wound is enhanced by keeping the wound bed moist. Thus a wound dressing should absorb and transfer wound exudate away from the wound surface without desiccating the wound bed. Additionally, the wound dressing should release from the wound easily without causing damage to the newly formed tissue.

Although the fibrous alginate wound dressings mentioned above perform these functions well, there are many inherent disadvantages associated with their use. Except for the knitted Ultraplast TM wound dressing, each of the aforementioned commercial alginate products is difficult to handle. The Steriseal Sorbsan TM dressing has poor structural integrity and tends to shed fibers when dry. Because of this weakness, skill is required to apply the dressing to wounds, and handling problems are aggravated when ones fingers are not completely dry. The Kaltostate TM dressing has better structural integrity but has a relatively high basis weight of about 160 g/m² and is not as supple as would be desired for most applications. Additionally, because alginate fibers are highly absorbent, dressings based on high basis weight webs of the fibers are more likely to desiccate a wound if applied to the wound in a dry condition. The manufacturer of the needle-tackled Kalostat TM dressing avoids this problem by recommending that the dressing be moistened before application to the wound.

Although the knitted Ultraplast TM wound dressing has good integrity when dry, it becomes weak and loses its integrity when saturated with saline or body fluids. This loss of integrity causes the Ultraplast TM wound dressing to disintegrate while being lifted from a wound (as do others of the commercial alginate dressings cited above), necessitating that it be picked out in tiny pieces or removed from the wound by irrigation. Because removal by irrigation is a complicated and messy process that requires a substantial degree of skill, users prefer wound dressings that can be lifted from a wound in a single piece.

Nonfibrous alginate wound dressings are also known in the art. For example, U.S. Pat. No. 4,393,048 (Mason, Jr. et al.) discloses a wound dressing comprising a water-soluble hydrogel of alkali metal alginate and glycerin. These wound dressings are said to be prepared by applying a gel composed of water, alkali metal alginate and glycerin to a wound, and allowing the composition to air dry to form a water-soluble flexible film. It is stated to be an advantage of these dry film dressings that they are water-soluble and can be removed by water washing. However, as stated above, water washing is messy and is less desirable than removing the dressing from the wound in one piece. Furthermore, these wound dressings probably do not function well in highly exuding wounds where it would likely take an unreasonably long period of time for the material to air dry; if such air drying can be accomplished at all.

Additionally, Swedish Patent Application Publication No. 424,956, published Aug. 23, 1982, discloses a water-insoluble alginate hydrogel wound dressing. This dressing is said to be prepared by mixing water-soluble alginate, a soluble metal salt having metal ions that react with the water-soluble alginate to form a crosslinked water-insoluble alginate, and water to form a reactive cream-like paste that is spread over the wound surface. After application to the wound surface the constant progression of the crosslinking reaction transforms the cream-like paste into an elastic rubber-like composition. It is stated that because of the dressing's composition it will have a fluid absorbing effect after it is converted into the elastic condition, and will evaporate moisture from its outer surface. While these properties are generally desirable in a wound dressing, the absorption of fluid by the disclosed hydrogel dressing must either be limited by the evaporation of fluid from the gel surface or must be accompanied by an undesirable swelling of the gel. If the absorbency of these dressings is controlled by the evaporation of fluid from the dressing surface, these dressings will be of limited utility for heavily exuding wounds as their absorbency will probably be too low to prevent a build up of wound exudate at the wound surface. If the dressing swells upon the absorption of fluids, this lack of dimensional stability may severely undercut the utility of these dressings for packing deep, heavily exuding wounds. When a deep, heavily exuding wound is packed with this gel the swelling which may accompany the absorption of fluid may cause the dislodging of the packing, unless the packing is restrained within the wound by an outer wrap of some form. However, if the gel is so restrained that it cannot swell, the fluid absorbing properties may be undesirably reduced.

SUMMARY OF THE INVENTION

The present invention provides a novel nonfibrous alginate wound dressing which absorbs wound exudate and releases easily from wound tissue without causing further damage to the wound and prolonging the healing process.

The wound dressing of the invention is a water-insoluble alginate hydrogel foam comprising approximately 95% water. The hydrogel foam of the invention is dimensionally stable and absorbs wound exudate without any appreciable swelling. Additionally, since the wound dressing is a hydrogel, it absorbs the wound exudate while maintaining a moist wound bed which promotes healing. Furthermore, the wound dressing of the invention has sufficient structural integrity to be lifted from a wound in one piece even though it has become saturated with blood or other saline fluids.

The wound dressing foam of the invention is formed in situ by applying a reactive gel-forming composition directly to the wound site. The reactive gel-forming composition comprises: (a) an aqueous solution of water-soluble alginate, (b) water-soluble acid dissolved therein, (c) particles of a water-insoluble di- or trivalent metal salt that will react with an acid to form a water-soluble metal salt, and which has a di- or trivalent metal ion capable of complexing with the pendant carboxylate groups of said water-soluble alginate to form a water-insoluble alginate hydrogel, suspended therein, and (d) an effervescent compound which effervesces upon reaction with an acid.

The reactive gel-forming composition foams as it gels. When applied in or on a wound, the foaming action gently expands the dressing material conforming it to the shape of the cavity in, or the surface on, which it is applied. The dressing material subsequently cures to a dimensionally stable hydrogel foam which exactly fits the wound.

The wound dressings of the invention have many applications in the fields of human and veterinary medicine. These form-in-place dressings are particularly useful for application in deep wounds such as grade III or IV dermal ulcers and burns which require packing to hold the wound edges apart for proper healing. These dressings may also be useful for problem wounds such as grade I, II, III, and IV dermal ulcers and burns which have impaired healing, since the alginate component may actually stimulate desirable cellular responses such as fibroplasia, angiogenesis and epithelialization. Furthermore, these hydrogel dressings can also be used as a vehicle for the sustained release of medicaments which enhance healing, such as growth factors and antimicrobials, to the wound site simply by inclusion of these medicaments into the gel-forming composition.

DETAILED DESCRIPTION OF THE INVENTION

The wound dressing of the invention comprises a hydrogel foam composed of one or more of the water-insoluble alginates, which include, with the exception of magnesium, the alkaline earth metal salts and the group III metal salts of alginic acid. The hydrogel foam is formed by mixing together a first liquid component (Component A) comprising an aqueous suspension of particles of a water-insoluble di- or trivalent metal salt, and an effervescent compound which effervesces upon reaction with an acid; and a second liquid component (Component B) comprising an aqueous solution of a biocompatible, water-soluble acid; wherein at least one of Components A and B further comprise water-soluble alginate dissolved therein. It is preferred that the water-soluble alginate be dissolved in Component A, and more preferred that the water-soluble alginate be dissolved in both Component A and Component B.

Upon mixing, the water-insoluble metal salt reacts with the water-soluble acid to form a water-soluble metal salt that is subsequently ionized. The polyvalent cations released from the water-soluble metal salt complexes with the pendant carboxylate groups of the water-soluble alginate causing the formation and precipitation of a water-insoluble alginate hydrogel. At the same time, the effervescent compound is reacting with the water-soluble acid with the resultant evolution of gases which become entrapped in the forming gel network, causing the formation of a stable hydrogel foam.

The water-soluble alginates useful in the formation of the wound dressing of the present invention include the ammonium, magnesium, potassium, sodium and lithium salts of alginic acid. The preferred water-soluble alginate is sodium alginate.

The water-insoluble di- or trivalent metal salts useful in the formation of the wound dressing of the invention must satisfy two requirements. First, the metal salt must contain a di- or trivalent metal ion capable of complexing with the pendant carboxylate groups of the water-soluble alginate to cause the formation of a water-insoluble alginate hydrogel. Second, the water-insoluble metal salt must react with the water-soluble acid to form a water-soluble metal salt. Preferred water-insoluble metal salts useful in the present invention include calcium carbonate, calcium phosphate dibasic ($CaHPO_4$), barium carbonate and zinc carbonate, with calcium carbonate being most preferred.

The biocompatible, water-soluble acid useful in the present invention may be chosen from monocarboxylic and dicarboxylic acids. Examples of suitable acids include acetic, lactic, malic, gluconic and ascorbic acids.

The effervescent compound used in the present invention must effervesce upon reaction with the water-soluble acid. Useful effervescent compounds may be chosen from the alkali metal carbonates with sodium carbonate being preferred.

Although recited as separate elements of Component A, it should be understood that in some cases the water-insoluble di- or trivalent metal salt and the effervescent compound may both be provided by a single compound. For example, the preferred water-insoluble metal salt (calcium carbonate) releases carbon dioxide gas upon reaction with the acid in Component B and, thus, produces a hydrogel foam without the inclusion of any other effervescent compounds. The resultant foam, however, generally has a relatively high density and low void volume due to the small amount of carbon dioxide typically produced by this reaction. Thus, even if the water-insoluble di- or trivalent metal salt effervesces, it may still be desirable to include an additional effervescent compound in order to obtain a hydrogel foam having a greater void volume and lower density.

The wound dressing of the invention is formed-in-place in the wound cavity, or on the wound surface, simply by mixing Component A with Component B and applying the reactive composite mixture directly to the wound site. After application of the composite to the wound site, gel formation occurs with the accompanying foaming action expanding the material and conforming it exactly to the shape of the cavity or the surface to which it was applied. The dressing subsequently cures to a dimensionally stable hydrogel foam that exactly fits the wound.

The rate of cure is governed by the rate of the reaction between the water-soluble acid and the water-insoluble metal salt and is thus controlled by the amounts of the metal salt and acid in the solution. Cure times ranging from one minute to several minutes have been observed and can be reproduced.

In practice, these form-in-place wound dressings can be prepared from a self-contained hydrogel-foam-forming article comprising a first chamber containing Component A, a second chamber containing Component B, and a means connected to said first and second chambers for intermixing Components A and B without exposing them to the atmosphere or to any external mixing devices. One example of such an article is a closed bag divided into two compartments by a removable closure, with Component A contained within the compartment on one side of the closure and Component B contained within the compartment on the opposite side of the closure. In this embodiment of the article, mixing of the two components can be accomplished simply by removing the closure and manually forcing the two components together.

Another example of such an article comprises two permanently separated component-containing chambers wherein each component-containing chamber is equipped with a discharge opening leading to a common mixing chamber. In this embodiment of the article, mixing of the two components can be accomplished by forcing each of the components from their respective chambers into the mixing chamber. Preferably the mixing chamber is in the form of a baffled discharge tube so that the components are mixed as they are discharged from the article through the discharge tube. A useful example of such an article is a double barrel syringe assembly equipped with a standard mixing tip.

As used herein, "double barrel syringe assembly" refers to a syringe having two separate barrels arranged side by side. Each barrel is equipped with a separate plunger to force the material contained therein out through a discharge opening. One end of each plunger is inside its respective barrel and forms a seal with the walls of the barrel. The other end of each plunger is outside of its respective barrel so that force from an external source can be applied to the plunger. The two plungers can be connected together at their ends outside of the barrels so that force exerted on the plungers will generate the same pressure within each barrel, and will displace both plungers an equal distance.

The hydrogel-foam-forming article is thus a self-contained unit having all of the reactive hydrogel-foam-forming materials enclosed therein, and is equipped with a mixing means capable of mixing the hydrogel-foam-forming components without exposing them to the atmosphere or to any external mixing devices. Thus, the user of the article can form the wound dressing without adding any additional materials to the enclosed ingredients, without exposing the enclosed ingredients to the atmosphere, the hands of the user or any mixing implements. Accordingly, there is no opportunity for adding too much or too little material, no requirement of a mixing vessel or mixing instrument, and no opportunity for contamination of the material during mixing. Therefore, if the chambers of the article are sterile prior to being filled with sterile hydrogel-foam-forming components, the article can produce sterile water-insoluble alginate hydrogel foam wound dressings.

The wound dressing of the invention is further illustrated by the following non-limiting examples wherein all percentages are by weight unless otherwise specified.

EXAMPLE 1

The alginate hydrogel foam wound dressing of Example I was prepared as follows:

(1) Component A was prepared by combining 3.8 g of sodium alginate (commercially available from Protan Inc. of North Hampton, N.H., under the trade designation Protanal LF 20/60), 1.9 g of sodium carbonate and 84.0 g of deionized water; stirring the combination until homogeneous; and then adding 0.5 g of calcium carbonate;

(2) Component B was prepared by combining 3.8 g of the same sodium alginate used in the preparation of Component A with 80.0 g of deionized water, at room temperature; stirring until the alginate was completely dissolved; and then adding 2.4 g of acetic acid;

(3) Components A and B were loaded, in equal volumes, into separate barrels of a double-barrel mixing syringe assembly fitted with a 3-inch, 6-turn mixing tip; and (4) Components A and B were discharged through the mixing tip of the mixing syringe into three vials of known and equal volume and allowed to foam and cure. The vials were filled to overflowing, and as soon as the foaming action subsided, any material exceeding the volume of the vials was removed.

EXAMPLES 2–12

The alginate hydrogel foam wound dressings of Examples 2–12 were prepared by the same method and from the same reactants used in the preparation of the alginate hydrogel foam of Example 1. The preparation of the alginate hydrogel foams of Examples 2–12 differs from the preparation of the foam of Example 1 only in the amounts of the calcium carbonate, sodium carbonate and acetic acid used. Therefore, as in Example 1, three samples of each of the hydrogel foams of Examples 2–12 were prepared. The amounts, in grams, of the reactants used to prepare the foams of Examples 1–12 are shown in Table I.

TABLE I

| Ex. No. | Component A | | | | Component B | | |
|---|---|---|---|---|---|---|---|
| | Water | Sodium Alginate | Sodium Carbonate | Calcium Carbonate | Water | Sodium Alginate | Acetic Acid |
| 1 | 84.0 | 3.8 | 1.9 | 0.5 | 80.0 | 3.8 | 2.4 |
| 2 | 84.0 | 3.8 | 1.9 | 0.5 | 80.0 | 3.8 | 3.0 |
| 3 | 84.0 | 3.8 | 1.9 | 0.5 | 80.0 | 3.8 | 3.6 |
| 4 | 84.0 | 3.8 | 1.9 | 1.0 | 80.0 | 3.8 | 2.7 |
| 5 | 84.0 | 3.8 | 1.9 | 1.0 | 80.0 | 3.8 | 3.3 |
| 6 | 84.0 | 3.8 | 1.9 | 1.0 | 80.0 | 3.8 | 4.2 |
| 7 | 84.0 | 3.8 | 1.9 | 2.0 | 80.0 | 3.8 | 3.3 |
| 8 | 84.0 | 3.8 | 1.9 | 2.0 | 80.0 | 3.8 | 4.2 |
| 9 | 84.0 | 3.8 | 1.9 | 2.0 | 80.0 | 3.8 | 4.9 |
| 10 | 84.0 | 3.8 | 1.9 | 2.0 | 80.0 | 3.8 | 2.5 |
| 11 | 84.0 | 3.8 | 1.9 | 2.0 | 80.0 | 3.8 | 1.7 |
| 12 | 84.0 | 3.8 | 0 | 1.3 | 80.0 | 3.8 | 1.7 |

The time required for the production of a cured hydrogel foam was measured for each sample of each of the examples. In this regard cure time represents the time elapsed between the mixing of Components A and B and the point at which no further changes in the tackiness of the foam were detectable by touch. The average cure times for the three samples of each of the hydrogel foams produced in Examples 1–12 are shown in Table II.

TABLE II

| Example No. | Cure Time (minutes) |
|---|---|
| 1 | 22.7 |
| 2 | 10.7 |
| 3 | 7.7 |
| 4 | 6.7 |
| 5 | 4.7 |
| 6 | 3.3 |
| 7 | 2.3 |
| 8 | 2.0 |
| 9 | 1.5 |
| 10 | 3.0 |
| 11 | 50.0[1] |
| 12 | 1.0 |

[1] cure time measurements terminated with hydrogel foam still in tacky state.

In the application of wound dressings minimizing the dressing application time is highly desired since this reduces nursing time and the inconvenience to the patient. Likewise, in the present invention reducing the cure time of the hydrogel foam is generally desirable. However, the cure time of the hydrogel must be of sufficient duration to allow the hydrogel forming solution to be applied to the wound site prior to the gelling and foaming activity. Preferably the hydrogel foam forms and cures in a period of from about 2 to 5 minutes.

As shown in Tables I and II, the cure time can be regulated via the concentration of the acid in Component A and the amount of polyvalent metal salt suspended in Component B. Cure times decrease as the concentration of the acid in Component A is increased and as the amount of the polyvalent metal salt suspended in Component B is increased. While varying the amount of either reactant can be used to control the cure time, it is preferable to use the minimum amount of acid necessary and regulate the cure time via the amount of metal salt present, since excessive acidity may have undesirable effects on the tissue compatibility of the mixture. Accordingly, the composition of Example 10, which produced a cured hydrogel foam in 3.0 minutes, and which had the lowest acid concentration of any of the compositions producing cured hydrogel foams within the desired range of cure times, is preferred over the other compositions tested.

Additionally, the density of the hydrogel foams produced in Examples 1–11, and the absorbency of the hydrogel foams produced in Examples 1–10 and 12 were measured. These are recorded in Table III. The recorded density and absorbency reflects the average for the three samples made in each example.

TABLE III

| Example No. | Density (g/cm3) | Absorbency (%) |
|---|---|---|
| 1 | 0.38 | 62 |
| 2 | 0.31 | 66 |
| 3 | 0.29 | 68 |
| 4 | 0.33 | 56 |
| 5 | 0.30 | 49 |
| 6 | 0.28 | 49 |
| 7 | 0.30 | 71 |
| 8 | 0.29 | 43 |
| 9 | 0.29 | 27 |
| 10 | 0.34 | 147 |
| 11 | 0.57 | — |
| 12 | | 8 |

The density was calculated simply by removing the foam sample from the vial, weighing it and dividing the weight by the volume of the vial.

The absorbency was measured by immersing the foam samples in a 0.9 weight percent solution of sodium chloride in water. After 24 hours, the test samples were removed from the solution, the excess solution on the surface of the samples was removed by blotting, and the samples were weighed. The absorbencies recorded in Table III reflect the weight of the saline solution absorbed as a percentage of the initial weight of the sample, and were calculated by dividing the difference in the weight of the sample before and after immersion in the saline solution by the initial weight of the sample.

The absorbency data recorded in Table III demonstrates that the ability of the hydrogel foam to absorb saline fluids is related to the void volume of the foam. The low void volume foam of Example 12, prepared without sodium carbonate, had a much lower absorbency than the higher void volume foams prepared in Examples 1–10.

EXAMPLE 13

Application of wound dressing to wound of test subject.

(A) Preparation of Test Subject:

A female Hartley Guniea Pig weighing 700 g was anesthetized with Halothane and its back was shaved and prepared for surgery. A one-inch, full-thickness incision was made at mid back, perpendicular to the spine. Using a small pair of forceps, the dermis adjacent to the incision was detached from the underlying fascia to create a pocket approximately one inch wide by two inches long.

(B) Preparation of Foam-Forming Components:

Component A was prepared by adding 3.8 g of sodium carbonate and 7.65 g of sodium alginate (commercially available from Protan Inc. of North Hampton, N.H., under the trade designation Protanal LF 20/60) to a suspension of 1.9 g of calcium carbonate in 167 g of deionized water, and stirring vigorously until a homogeneous suspension was achieved.

Component B was prepared by adding 7.6 g of the same sodium alginate used in Component A to a solution of 6.5 g of glacial acetic acid in 161 g of deionized water, and stirring vigorously until a homogeneous mixture was achieved.

Components A and B were loaded, in equal volumes, into separate barrels of a double barrel mixing syringe assembly fitted with a 3-inch, 6-turn mixing tip.

(C) Application to the Wound:

While holding the incision open, the components described above were discharged from the syringe through the mixing tip, and the composite material was applied to the wound in a quantity sufficient to completely fill the pocket between the dermis and the fascia when the mixture had completely foamed. When the hydrogel foam had cured completely, most of it was covered by dermis except for a portion located directly under the incision where the profile of the hydrogel held the wound edges apart. A Tegaderm TM dressing was then applied over the incision.

Nineteen hours after the surgery and application of the form-in-place alginate hydrogel foam wound dressing, the subject displayed no evidence of discomfort and the skin covering the dressing was normal in color, with no redness observed. No accumulation of exudate outside the wound was evident, and the edges of the wound appeared to be moist.

The subject was sacrificed 19 hours after surgery and the skin covering the wound dressing was excised to reveal the hydrogel. The hydrogel foam was intact, and was easily removed in one piece. Judging by the foam's color and lack of air pockets the foam appeared to have absorbed wound exudate. Additionally, no evidence of irritation to the surrounding tissue was observed.

What is claimed is:

1. A method of making, in situ, a water-insoluble alginate hydrogel foam wound dressing comprising the steps of:
   (I) mixing together, to form a composite liquid mixture, a first liquid component comprising: (a) an aqueous suspension of particles of a water-insoluble di- or trivalent metal salt that will react with an acid to form a water-soluble metal salt, and which has a di- or trivalent metal ion capable of complexing with pendant carboxylate groups on water-soluble alginates to form water-insoluble alginate hydrogels, and (b) an effervescent compound which effervesces upon reaction with an acid; and a second liquid component comprising an aqueous solution of a biocompatible, water-soluble acid, wherein at least one of said components further comprise water-soluble alginate dissolved therein;
   (II) applying said composite liquid mixture directly to a wound site; and
   (III) allowing said composite liquid mixture to react.

2. A method of making, in situ, a water-insoluble alginate hydrogel foam wound dressing comprising the steps of:
   (I) mixing together a first liquid component comprising: (a) water, (b) water-soluble alginate, (c) water-insoluble di- or trivalent metal salt that will react with an acid to form a water-soluble metal salt, and which has a di- or trivalent metal ion capable of complexing with pendant carboxylate groups on said water-soluble alginate to form a water-insoluble alginate hydrogel, and (d) an effervescent compound which effervesces upon reaction with an acid; and a second liquid component comprising an aqueous solution of a biocompatible, water-soluble acid, to form a composite liquid mixture;
   (II) applying said composite liquid mixture directly to a wound site; and
   (III) allowing said composite liquid mixture to react.

3. The method of making, in situ, a water-insoluble alginate hydrogel foam wound dressing as recited in claim 2 wherein said water-soluble alginate is selected from the group consisting of the ammonium, magnesium, potassium, sodium, and lithium salts of alginic acid.

4. The method of making, in situ, a water-insoluble alginate hydrogel foam wound dressing as recited in claim 2 wherein said water-soluble alginate is selected from the group consisting of sodium alginate and potassium alginate.

5. The method of making, in situ, a water-insoluble alginate hydrogel foam wound dressing as recited in claim 2 wherein said water-insoluble di- or trivalent metal salt is selected from the group consisting of calcium carbonate, calcium phosphate dibasic, barium carbonate and zinc carbonate.

6. The method of making, in situ, a water-insoluble alginate hydrogel foam wound dressing as recited in claim 2 wherein said water-insoluble divalent metal salt is calcium carbonate.

7. The method of making, in situ, a water-insoluble alginate hydrogel foam wound dressing as recited in claim 2 wherein said biocompatible, water-soluble acid is selected from the group consisting of acetic, lactic, malic, gluconic, and ascorbic acids.

8. The method of making, in situ, a water-insoluble alginate hydrogel foam wound dressing as recited in claim 2 wherein said second component further comprises water-soluble alginate.

9. The method of making, in situ, a water-insoluble alginate hydrogel foam wound dressing as recited in claim 8 wherein the water-soluble alginate in both said first and second components is of the same composition.

10. The method of making, in situ, a water-insoluble alginate hydrogel foam wound dressing as recited in claim 9 wherein said water-soluble alginate is selected from the group consisting of sodium alginate and potassium alginate.

11. The method of making, in situ, a water-insoluble alginate, hydrogel foam wound dressing as recited in claim 2 wherein said effervescent compound is selected from the group consisting of the alkali metal carbonates.

12. The method of making, in situ, a water-insoluble alginate, hydrogel foam wound dressing as recited in claim 2 wherein said effervescent compound is sodium carbonate.

13. An alginate hydrogel foam wound dressing prepared by the method of claim 1.

14. An alginate hydrogel foam wound dressing prepared by the method of claim 2.

15. An alginate hydrogel foam, wound dressing prepared by the method of claim 3.

16. An alginate hydrogel foam wound dressing prepared by the method of claim 4.

17. An alginate hydrogel foam wound dressing prepared by the method of claim 5.

18. An alginate hydrogel foam wound dressing prepared by the method of claim 10.

19. An alginate hydrogel foam wound dressing prepared by the method of claim 7.

20. An hydrogel foam wound dressing prepared by the method of claim 8.

21. An alginate hydrogel foam wound dressing prepared by the method of claim 13.

22. An alginate hydrogel foam wound dressing prepared by the method of claim 10.

23. An alginate hydrogel foam wound dressing prepared by the method of claim 11.

24. An alginate hydrogel foam wound dressing prepared by the method of claim 12.

25. A method of making, in situ, a water-insoluble alginate hydrogel foam wound dressing comprising the steps of:
   (I) mixing together a first liquid component comprising: (a) water, (b) sodium alginate, (c) calcium carbonate, and (d) sodium carbonate; and a second liquid component comprising: (e) water, (f) acetic acid, and (g) sodium alginate, to form a composite liquid mixture;
   (II) applying said composite liquid mixture directly to a wound site; and
   (III) allowing said composite liquid mixture to react.

26. An alginate hydrogel foam wound dressing prepared by the method of claim 25.

27. An alginate hydrogel foam wound dressing made by the process comprising the steps of:

(I) mixing together, to form a composite liquid mixture, a first liquid component comprising: (a) an aqueous suspension of particles of a water-insoluble di- or trivalent metal salt that will react with an acid to form a water-soluble metal salt, and which has a di- or trivalent metal ion capable of complexing with pendant carboxylate groups on water-soluble alginates to form water-insoluble alginate hydrogels, and (b) an effervescent compound with effervesces upon reaction with an acid; and a second liquid component comprising an aqueous solution of a biocompatible, water-soluble acid, wherein at least one of said components further comprise water-soluble alginate dissolved therein;

(II) applying said composite liquid mixture directed to a wound site; and (III) allowing said composite liquid mixture to react.

* * * * *